United States Patent [19]

Okuyama et al.

[11] Patent Number: 4,767,624

[45] Date of Patent: Aug. 30, 1988

[54] DECUBITAL REMEDY

[76] Inventors: Shinichi Okuyama, 15-38 Nakayama 3-chome, Sendai-shi, Miyagi Prefecture; Kazumaro Furuse, 3-5, Inogashira 2-chome, Mitaka-shi, Tokyo; Shigemitsu Ohsawa, 2286-12, Suehiro-cho, Honjyo-shi, Saitama Prefecture, all of Japan

[21] Appl. No.: 838,559

[22] Filed: Mar. 11, 1986

[30] Foreign Application Priority Data

Mar. 15, 1985 [JP] Japan ................................ 60-50543

[51] Int. Cl.[4] ............................................ A61K 37/48
[52] U.S. Cl. .................................................. 424/94.1
[58] Field of Search ................................. 424/94, 94.1

[56] References Cited

U.S. PATENT DOCUMENTS 4,031,265  6/1977  Konishi .............................. 424/94
4,073,883  2/1978  Yasuda et al. ..................... 424/94

FOREIGN PATENT DOCUMENTS 2472384  7/1981  France .
0649917  3/1982  Switzerland ..................... 424/94

OTHER PUBLICATIONS

Chem. Abst. 94:162784b, 1981.
Chem. Absts. 88:27812v; 27813w; 27814x; 27815y; 27816z.

*Primary Examiner*—John Rollins

[57] ABSTRACT

A decubital remedy suitable for cutaneous administration contains ubidecarenone as an effective ingredient. The decubital remedy, which may preferably take the form of a cream, lotion or ointment, is effective in reducing decubitus-related severe pain and restoring the tissue damaged by decubitus. It is applicable even to patients who are unable to take drugs orally by themselves due to dyscrasia or cranial nerve disorders. It is also free of such cumbersomeness and body-wide influence as injection.

1 Claim, No Drawings

DECUBITAL REMEDY

BACKGROUND OF THE INVENTION

1. Field of the Invention

The present invention relates to a decubital remedy which contains ubidecarenone as an effective or active ingredient. Namely, this invention is directed to a novel utility of ubidecarenone as a pharmaceutical product. It is useful for the treatment of decubitus in the therapeutic field.

2. Discussion of the Background

Decubitus means ischemic necrosis of the skin or subcutaneous tissue caused at a projected bone area due to continuous pressure. It is a problem annoying many patients who suffer from chronic diseases, especially, such as patients of cancers and lesions of cerebral vessels. Depending on causes, decubitus may be roughly divided into paralytic decubitus and non-paralytic decubitus. The former is induced by damage to the spinal cord, ulcer, infection, degenerative disease or the like. The latter is developed in aged patients as a result of such patients being confined to their beds over long periods of time, and also by chronic anemia and malnutrition, and by compression in plaster upon fracture.

For the prevention or treatment of decubitus, it is the practice to change the position of a patient or to release one or more pressed areas of the patient from pressure so that his skin is protected from continuous compression. It is also the practice to use a special bed making use of a good hygroscopic cushioning material and to effect rigorous skin cleaning and wiping, thereby ensuring keeping the skin dry for the prevention of secondary infection. Furthermore, it is also the practice to improve and control the nutrition or to treat anemia with a high-protein and high-calory diet. Where the condition of decubitus is extremely serious, surgery is effected to resect the decubital part and then to restore the resulting lost part by sutured minification, adjacent flap, distant flap or the like. Decubitus however still remains as a hardly-curable and difficult skin disease, resulting is long and severe pain to patients.

SUMMARY OF THE INVENTION

With the foregoing in view, the present inventors have carried out various investigations with a view toward achieving the treatment of decubitus by administration of drugs.

As disclosed in the following publications (1) and (2), the present inventors previously used ubidecarenone on a trial bases for the treatment of radiation dermatitis or radiation ulcers, leading to recognition of superb effectiveness of ubidecarenone.

(1) Okuyama, S. and Mishina, H.: Principia of cancer therapy, I. Rescue of radiation damage, Sci. Rep. Res. Inst. Tohoku Univ.-C 29: 1, 1982); and (2) Okuyama, S. and Mishina, H.: Principia of cancer therapy, VI. Application of ubiquinone ointment for intractable radiation ulcers: An expanded cytochrome c effect? Sci. Rep. Res. Inst. Tohoku Univ.-C 30: 36, 1983).

It was of course impossible to foresee whether ubidecarenone would show similar significant effects on decubitus, because decubitus is different in cause and condition from radiation dermatitis or radiation ulcers.

The present inventors have proceeded with further investigations. As a result, it has been found that significant curative results can be obtained by a direct coating application of ubidecarenone to areas affected by decubitus, leading to completion of this invention.

This invention thus provides a decubital remedy suitable for cutaneous administration, which comprises ubidecarenone as an effective ingredient.

The decubital remedy of this invention, which may preferably take the form of a cream, lotion or ointment, is effective in reducing decubitus-related severe pain and restoring the tissue damaged by decubitus.

The above and other objects, features and advantages of this invention will become apparent from the following detailed description and the appended claims.

DETAILED DESCRIPTION OF THE INVENTION AND PREFERRED EMBODIMENTS

The term "decubitus" as used herein should be interpreted in a broad sense. Describing in brief, it means ischemic necrosis of the skin or subcutaneous tissue caused at a projected bone area due to continuous pressure.

Next, ubidecarenone is also called "ubiquinontene" or "coenzyme $Q_{10}$". Ubidecarenone which has conventionally been used as a therapeutic agent for congestive heart failure may also be used in the present invention as is. Ubidecarenone is extracted from mitochondria of bovine heart muscle and is known to take part in the electron transport system. Ubidecarenone can therefore improve the percent oxygen utilization in heart muscle and hence maintain the ATP-yielding function as a high level even if the heart muscle is in an ischemic state. As a result, ubidecarenone is known to reduce the damage, which the ischemic cardiac muscular tissue undergoes, and to improve the lowering of the heart construction function.

However, the fact that decubitus can be effectively cured with cutaneously-applied ubidecarenone has been unknown to date. It has been found for the first time by the present inventors.

Ubidecarenone is crystalline powder of a yellow or orange color, the melting point of which is 48°–52° C. It is oil-soluble but is scarcely soluble in water or methanol. As described above, it has been orally administered in order to improve various symptoms of congestive heart failure. For the sake of reference, its subacute toxicity and chronic toxicity upon its oral administration are as follows: Subacute toxicity:

Ubidecarenone was continuously and orally administered to male and female Wistar rats at doses of 40, 200 and 1,000 mg/kg/day for 5 weeks and to male and female rabbits at doses of 60 and 600 mg/kg/day for 23 days. Neither rats nor rabbits developed any difference compared with their respective controls in general conditions, blood test, urine test and morphological observation (both visual and histological).

Chronic toxicity:

Ubidecarenone was forcedly and orally administered to male and female Wistar rats at doses of 6, 60 and 600 mg/kg/day for straight 26 weeks.

The present invention features cutaneous administration of ubidecarenone to an area where decubitus, defined as described above in the present invention, has been developed.

Upon cutaneous administration, ubidecarenone may be applied directly. It is however desirable to apply it as a preparation suitable for skin coating if possible. Ubidecarenone may be administered along with one or more other drugs, for example, cytchrome c, urokinase and/or the like. It should however be borne in mind that the present invention is not necessarily limited to or by such a combined administration.

As the content of ubidecarenone in the remedy of this invention, the content may be recommended as 0.05–5.0% with 0.1–2.0% being more preferable. The remedy may be coated in an amount suitable depending on the size and severity of each decubitus-affected area.

Ubidecarenone shows good stability upon its cutaneous administration and gives low irritation to the skin. Table 1 shows, by way of example, results of various tests of ubidecarenone on primary cutaneous irritation, cumulative irritation, blepharo-irritation, phototoxicity, challenge and optical challenge as well as results of its patch test.

| Property | Concentration | Solvent | Results and Conclusion | |
|---|---|---|---|---|
| Primary cutaneous irritation | 1% | squalane | 0.1 | low skin irritation |
| | — | " | 0.1 | |
| Cumulative irritation | 1% | " | 0.3 | low skin irritation |
| | — | " | 0.3 | |
| Blepharo-irritation | 1% | " | | low blepharo-irritation |
| | — | " | | |
| Phototoxicity | 1% | " | (—) | low phototoxicity |
| | 10% | " | (—) | |
| Challenge | Induction: 5% acetone | | | |
| (Adjuvante & patch method) | 5% | acetone | 0/10 | low challenge |
| | 1% | " | 0/10 | |
| Optical challenge | Induction: 10% acetone | | | |
| (Adjuvante & strip method) | 10% | acetone | 0/5 | |
| | 5% | " | 0/5 | |
| | 2% | " | 0/5 | low optical challenge |
| | 1% | " | 0/5 | |
| | 0.5% | " | 0/5 | |
| Patch test | 1% | squalane | 0/54 | low skin irritation |
| | — | " | 0/54 | |

To form ubidecarenone into a preparation suitable for its cutaneous administration, one or more suitable low-irritant bases may be chosen as ingredient(s) other than ubidecarenone and then mixed with ubidecarenone. For example, glycerin, squalane, cetyl alcohol, yolk phospholipid, the glyceryl ester of a fatty acid and/or the like may be chosen. They may then be formulated into a preparation for cutaneous administration by a method known per se in the art.

Having generally described this invention, a further understanding can be obtained by reference to certain specific examples which are provided herein for purpose of illustration only and are not intended to be limiting unless otherwise specified.

EXAMPLE 1

| | wt. % |
|---|---|
| Stearyl alcohol | 12.0 |
| Squalane | 6.0 |
| Isopropyl myristate | 4.0 |
| Polyoxyethylenecetyl-alcohol ether (20 moles) | 3.0 |
| Stearic acid | 2.0 |
| Ubidecarenone | 0.5 |
| Propylene glycol | 6.0 |
| Ethylparaben | 0.1 |
| Butylparaben | 0.1 |
| Purified water | Balance to 100.0 |

The above-proportioned ingredients were mixed by a method known per se in the art to prepare a homogeneous cream as a remedy of this invention.

EXAMPLE 2

| | wt. % |
|---|---|
| Squalane | 15.0 |
| Octyldodecyl myristate | 5.0 |
| Hydrogenated soybean oil | 5.0 |
| Propylene glycol monostearate | 4.0 |
| Glycerin monostearate | 1.5 |
| Stearic acid | 2.0 |
| Ubidecarenone | 1.0 |
| Polyoxyethylene-hardened caster oil (50 moles) | 1.0 |
| Partially-hydrogenated yolk phospholipid | 1.0 |
| Glycerin | 5.0 |
| Ethylparaben | 0.3 |
| Antioxidant | as needed |
| Purified water | Balance to 100.0 |

The above-proportioned ingredients were mixed by a method known per se in the art to prepare a homogeneous cream as a remedy of this invention.

EXAMPLE 3

| | wt. % |
|---|---|
| Squalane | 3.0 |
| Octyldodecyl myristate | 2.0 |
| Stearic acid | 1.2 |
| Glycerin monostearate | 1.0 |
| Sorbitan monopalmitate | 0.5 |
| Cetyl alcohol | 0.5 |
| Cetyl alcohol monopalmitate | 0.5 |
| Polyoxyethylene glycerin monostearate (20 moles) | 1.5 |
| Methylparaben | 0.2 |
| Propylene glycol | 5.0 |
| Xanthan gum | 0.05 |
| Ubidecarenone | 0.3 |
| Perfume | as needed |
| Purified water | Balance to 100.0 |

The above-proportioned ingredients were mixed by a method known per se in the art to prepare a homogeneous lotion as a remedy of this invention.

EXAMPLE 4

| | wt. % |
|---|---|
| Partially-hydrogenated | 0.1 |

|  | wt. % |
| --- | --- |
| yolk phospholipid |  |
| Ubidecarenone | 0.1 |
| Macrogoal 400 | 4.0 |
| Ethyl alcohol | 8.0 |
|  | (vol.%) |
| Polyoxyethylene-hardened caster oil (50 moles) | 0.8 |
| Propylene glycol | 2.0 |
| Ethylparaben | 0.1 |
| Perfume | as needed |
| Antioxidant | as needed |
| Purified water | Balance to 100.0 vol.%. |

The above-proportioned ingredients other than the purified water were formed into a homogeneous solution while heating. The resulting solution was maintained at about 60° C., and was then poured with stirring into the purified water which had beforehand been heated to the same temperature. They were stirred into an intimate mixture and then cooled to room temperature, thereby preparing a ubidecarenone containing lotion as a remedy of this invention.

EXAMPLE 5

|  | wt. % |
| --- | --- |
| Solid paraffin | 1.0 |
| Microcrystalline paraffin | 7.0 |
| Cetyl alcohol | 2.0 |
| Aluminum stearate | 1.0 |
| Ubidecarenone | 1.0 |
| Liquid paraffin | 25.0 |
| White soft paraffin | Balance to 100.0 |

The above-proportioned ingredients were mixed by a method known per se in the art to prepare a homogeneous ointment as a remedy of this invention.

Effects of this invention will hereinafter be described by certain case reports. The effectiveness of the present invention was tested with respect to patients who had been admitted to the Radiology Department or the Circulatory Organ and Internal Department and were unable to change their positions by themselves due to their exhaustion for terminal cancers or severe lesions of cerebral vessels. Their life prognoses were absolutely hopeless. As a matter of fact, three out of the four cases resulted in death in 2-3 days or 4 months subsequent to the test. As a sample remedy of this invention, an ointment containing 0.5% of ubidecarenone was used. The treatment was effected by sterilizing each decubitus-affected area with "Hibiten" or "Pyrozosin", and then coating the ointment on the affected area.

Case No. 1:

37 Year old male. After surgery of a right seminoma, it transferred to the brain and orchiectomy was performed. The seminoma contained embrylonal cells and was hence a high-malignancy seminoma from the morphological viewpoint. In spite of postorchioctomical radiation, the cancer transferred subsequently to the peritoneum, lungs and brain. Acute decubitus occurred in the course of radiotherapy of the metastasized brain. He was unable to change his position by himself because he was also suffering from disturbance of consciousness. Decubitus was developed at the sacrum. In three days after the initiation of treatment with the ubidecarenone ointment, severe pain and erythema were both reduced and crust was formed, in other words, a promising sign of cure was observed. Three days later, the decubitus was cured completely.

Case No. 2:

69 Year old male. Due to recurrence of kidney cancer after its surgery, no further operation was feasible although its intraperitoneal dilatation was confirmed by celiotomy. Radiotherapy was applied in order to lighten severe pain at the lumboabdominal area. Infiltrated stomach wall was also confirmed as a result of a stomachal endoscopic test. His clinical condition aggravated due to hematemesis and fast, followed by development of decubitus at the sacrum. Immediately, treatment was started by applying the ubidecarenone ointment. The curing effect was remarkable and a promising sign of improvement was recognized shortly. However, the patient died 3 days later due to the original disease.

Case No. 3:

84 Year old male. After radiochemotherapy of esophagus cancer, the cancer transferred to the right cervix area. The right cervix area was subjected to radiochemotherapy which employed hyperthermia in combination. One year later, ulcer was formed at the right cervix area. Although it was not cancer in nature, he believed that it was recurrence of the cancer. In despair, he became like apositic. Since decubitus was developed at the sacrum, coating of the ubidecarenone ointment was started. It was steadily improved to complete cure.

Case No. 4:

84 Year old male. He developed disturbance of consciousness subsequent to cerebral infarct. Upon an elapsed time of half a year after the cerebral infarct, decubitus concentrating in the lower right back was observed. In spite of its treatment through coating of conventional therapeutic agents over 3 months, the condition was not improved. When treatment was started by using the ubidecarenone ointment of this invention, deep ulcer had already been formed and necrosic skin fragments remained as crust. When its treatment was started by coating the ubidecarenone ointment there, supply of blood took place promptly to start curing the ulcer. It was however observed that tissue components of necrosic skin fragments still remained there, coupled by *Pseudomonas aeruginosa* infection. Thus, a hydrogen peroxide solution and "Elace C" ointment were also used in combination. Then, its cure was accelerated, the ulcered skin area was rendered very small and its conversion into cuticule took place. Moreover, the treatment of scars was also promoted.

Decubitus is necrosis of a tissue caused by a hemokinetic trouble. As demonstrated in the above case reports, the reduction of severe pain and restoration of tissue can be both materialized by applying the ubidecarenone ointment. It has thus found that ointment, cream or lotion therapy, which makes use of ubidecarenone, exhibits superb effects.

The following three advantages may be mentioned as major advantages of the ointment, cream or lotion therapy.

(1) It is applicable even to patients who are unable to take drugs orally by themselves due to dyscrasia or cranial nerve disorders.

(2) It is free of such cumbersomeness and bodywide influence as injection.

(3) It is only necessary to coat a thin layer of a ubidecarenone ointment, cream or lotion when an affected area is disinfected.

The above-mentioned three features have extremely important significance for the treatment of decubitus.

Namely, when decubitus is induced, hemokinetic trouble generally accompanies. As a corollary to this, remarkable curing effects are usually unavailable even when its treatment is attempted by way of hemokinesis, for example, by oral administration or injection of a therapeutic drug. Oral administration is by itself difficult to perform especially when decubitus has been developed in the course of long-term treatment of a disease accompanied by disturbance of consciousness. It is here that ubidecarenone has the important significance, because the treatment of decubitus can be achieved by a simple external application of ubidecarenone. The outstanding clinical usefulness of this invention can be readily appreciated when one takes into consideration the fact that more and more patients of terminal cancers or neuraxial disorder are suffering from decubitus reflecting the increase in actual number of such patients.

It has also been confirmed through an additional investigation that the present invention can also exhibit sufficient preventive effects by its application when erythema has been induced and decubitus is about to occur. Accordingly, the usefulness of the present invention has also been confirmed in connection with prevention of decubitus.

It has also been found preferable to perform effective disinfection or sterilization to the affected skin, to use a histolytic agent in combination and/or to resect the affected skin, since skin infection, especially, skin narcosis with remaining myofilaments gives adverse influence in obtaining the curing effects of ubidecarenone.

Having now fully described the invention, it will be apparent to one of ordinary skill in the art that many changes and modifications can be made thereto without departing from the spirit or scope of the invention as set forth herein.

What is claimed is:

1. A method for the treatment of decubitus which comprises cutaneously applying to an affected area of a patient suffering therefrom an effective amount of ubidecarenone.

* * * * *